United States Patent [19]

Sieb et al.

[11] 4,179,445
[45] Dec. 18, 1979

[54] METHOD OF PREPARATION OF 2-PHOSPHATE ESTERS OF ASCORBIC ACID

[75] Inventors: Paul A. Sieb; Charles W. Deyoe; Russell C. Hoseney, all of Manhattan, Kans.

[73] Assignee: Kansas State University Research Foundation, Manhattan, Kans.

[21] Appl. No.: 911,669

[22] Filed: Jun. 1, 1978

Related U.S. Application Data

[63] Continuation of Ser. No. 817,555, Jul. 21, 1977, abandoned, which is a continuation of Ser. No. 683,888, May 6, 1976, abandoned.

[51] Int. Cl.$^2$ ................................................ C07F 9/09
[52] U.S. Cl. ............................ 260/340.9 R; 260/343.7
[58] Field of Search .................... 260/343.7, 340.9 R

[56] References Cited

U.S. PATENT DOCUMENTS

| | | | |
|---|---|---|---|
| 3,658,848 | 4/1972 | Nomura et al. | 260/343.7 |
| 3,671,549 | 6/1972 | Hinkley | 260/343.7 |
| 3,718,482 | 2/1973 | Hinkley | 99/150 |

FOREIGN PATENT DOCUMENTS

| | | | |
|---|---|---|---|
| 1805958 | 5/1969 | Fed. Rep. of Germany | 260/343.7 |
| 1201404 | 8/1970 | United Kingdom | 260/343.7 |
| 1201958 | 8/1970 | United Kingdom | 260/343.7 |

OTHER PUBLICATIONS

Cutolo et al., Gazz. Chim. Ital., vol. 91 (1961) pp. 964–972.
Chemical Abstracts, vol. 79, 66743 g, abstracting Jap. Pat. 73-15605, May 16, 1973.

*Primary Examiner*—Norma S. Milestone
*Attorney, Agent, or Firm*—Schmidt, Johnson, Hovey & Williams

[57] ABSTRACT

A method of preparing nutritionally useful 2-phosphated ester derivatives of ascorbic acid in extremely high yields is disclosed which includes steps of reacting an ascorbic acid such as L-ascorbic acid or a derivative such as 5,6-O-isopropylidene-L-ascorbic acid with a phosphorylating agent in the presence of a tertiary amine while maintaining the pH of the reaction mixture at a level of at least about 8 for achieving almost quantitative 2-phosphorylation of the ascorbic acid derivative. In preferred forms 5,6-O-isopropylidene-L-ascorbic acid is reacted in water with phosphorous oxychloride in the presence of about a fivefold excess of pyridine relative to the acid and at low temperatures ($-5$ to $+5°$ C.); an alkali metal hydroxide such as potassium hydroxide is added to the reaction mixture as needed for maintaining the pH thereof at a level of about 12–13 during the entire phosphorylation reaction. Production of the diester of the ascorbic acid derivative can be selectively increased by omitting the tertiary amine from the reaction mixture and conducting the reactant at an elevated temperature of from about 30°–60° C.

3 Claims, No Drawings

METHOD OF PREPARATION OF 2-PHOSPHATE ESTERS OF ASCORBIC ACID

This is a continuation of application Ser. No. 817,555 filed 7/21/77 which was, in turn a continuation of Ser. No. 683,888, filed May 6, 1976, both now abandoned.

This invention relates to a method of synthesizing monoascorbyl and diascorbyl 2-phosphates in order to produce phosphorylated derivatives which have utility as stable, nutritionally valuable sources of vitamin C which can be used in a wide variety of food systems. More particularly, it is concerned with a method of synthesis wherein an ascorbic acid derivative and a phosphorylating agent are reacted in the presence of a tertiary amine, with the pH of the reaction mixture being maintained at a relatively high level during the entire phosphorylation reaction; in this fashion, very high yields of the desired phosphorylated products are achieved, and analytically pure compounds are produced which can be used as vitamin C additives. If production of diascorbyl phosphate is desired, the tertiary amine can be omitted and the reaction temperature elevated.

L-ascorbic acid (vitamin C) is a vital part of a balanced human diet, and a recommended dietary allowance of this vitamin has been established. However, vitamin C is the least stable vitamin in foods since it is highly reactive with oxygen in air. For example, ascorbic acid is known to react rapidly with oxygen to give dehydroascorbic acid, a compound that retains full vitamin C activity, but which rapidly and irreversibly decomposes to compounds with no vitamin C potency. Ascorbic acid is also destroyed at high temperatures by dehydration in acidic media. Thus, efforts at directly incorporating L-ascorbic acid into doughs or batters which are subsequently baked or fried have proven ineffective, because only small amounts of vitamin C activity of the L-ascorbic acid does survive cooking at high temperatures. In other cases, the color of certain foods that would normally be considered excellent carriers of vitamin C are adversely affected by addition of ascorbic acid. For example, the pigments in cranberry juice fade upon addition of L-ascorbic acid, whereas an undesirable pink color develops when precooked potato flakes are sprayed with L-ascorbic acid. Neither of these undesirable color reactions would be expected using 2-phosphate esters of L-ascorbic acid, since this compound is not as powerful a reducing compound as is L-ascorbic acid.

It is known that ascorbic acid can be made more stable to oxygen and heat by converting it to selected chemical derivatives. In particular, inorganic esters on the 2-position of L-ascorbic acid, such as L-ascorbic 2-phosphate or L-ascorbate 2-sulfate, are not as easily oxidized as L-ascorbic acid. Additionally, the 2-phosphate and 2-sulfate derivatives of L-ascorbic acid are known to exhibit vitamin activity in animals which makes them attractive, stabilized derivatives of vitamin C which can be used to supplement the diet of fish, for example. It is believed that the 2-phosphate ester will be active in essentially all animals, since enzymes that are known to cleave phosphate ester groups are present in the digestive tracts of animals.

Several methods of synthesis of L-ascorbate 2-phosphate have been described in the past, and it has been demonstrated that the phosphate ester has, as expected, high vitamin C potency. For example, E. Cutolo and A. Larizza, *Gass. Chim. Ital.* 91 (1961) 964, demonstrated that guinea pigs excreted L-ascorbate in their urine when the animals were fed or injected with magnesium L-ascorbate 2-phosphate. The quantity of L-ascorbic acid excreted by the animals given L-ascorbate 2-phosphate was equal to the amount excreted by animals fed an equivalent amount of L-ascorbic acid. These results indicate that L-ascorbate 2-phosphate is converted quantitatively to L-ascorbate and inorganic phosphate in the gut. Similar results would be expected in man by virtue of the action of alkaline phosphatase in the digestive tract of humans.

Prior attempts at synthesizing analytically pure L-ascorbate 2-phosphate and derivatives thereof in commercially feasible yields have met with little success. Such prior work is described in the above identified publication of Cutolo et al., as well as that of Nomura et al *Chem. Pharm. Bull.,* 19 (7) (1971) 1433, U.S. Pat. No. 3,671,549 to Hinkley and German Pat. No. 1,805,958. In general however, the methods heretofore reported have achieved relatively low yields of the desired products or have failed to give analytically pure phosphate ester derivatives which can be used in food systems as vitamin C sources.

It is therefore the most important object of the present invention to provide a commercially feasible method of producing phosphated esters of ascorbic acid in good yield which can be easily recovered in an analytically pure state and used as vitamin C sources in food systems or vitamin premixes without fear that the phosphate esters will become deactivated by virtue of decomposition in the presence of oxygen or under high heat conditions.

As a corollary to the foregoing, another object of the invention is to provide a method of synthesizing the 2-monophosphate ester derivative of ascorbic acid which includes the steps of reacting an ascorbic acid or a derivative thereof such as L-ascorbic acid or 5,6-O-isopropylidene-L-ascorbic acid with a phosphorylating agent such as a phosphorous oxyhalide in the presence of a tertiary amine while maintaining the pH of the reaction mixture at a level of at least about 8 for achieving high yields of 2-phosphorylated derivatives of the starting reactant; in the most preferred form, L-ascorbate 2-phosphate is produced by reacting 5,6-O-isopropylidene-L-ascorbic acid, phosphorous oxychloride, and approximately a fivefold excess of pyridine relative to the acid in water at a temperature of from about −5 to +5° and in the presence of sufficient potassium, cesium or rubidium hydroxide to maintain the pH of the reaction mixture at a level of about 12 to 13 during the entire phosphorylation reaction.

Another object of the invention is to provide a method of synthesizing diascorbyl 2,2'-phosphate or its derivatives which in many respects is similar to the preferred process for producing monoascorbyl 2-phosphate but which differs in the omission of the tertiary amine and in the fact that the reaction is preferably conducted at an elevated temperature within the range of from about 30° to 60° C.; these reaction conditions serve to enhance the production of the diester products as opposed to the 2-phosphated monoester.

Broadly, the present invention is concerned with a method of preparing phosphorylated esters of ascorbic acid and includes the steps of admixing a first ascorbic acid reactant and a phosphorylating agent. The first reactant is preferably taken from the group consisting of ascorbic acid compounds which include a moiety of the formula

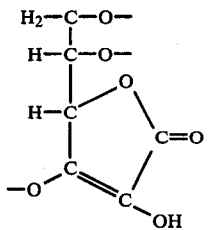   I.

and ascorbic acid compounds which include a moiety which is a stereoisomer of formula I above. The phosphorylating agent reacted with a compound of the above type is preferably of the formula $POX_3$   II.

where X is a halide, with the most preferred phosphorylating agent being phosphorous oxychloride.

The preferred reaction mixture also includes a quantity of a tertiary amine such as pyridine and the derivatives of pyridine. Although the lower trialkylamines, such as triethylamine, give results which are an improvement over the prior art, they are somewhat less preferred since some starting material remains unreacted when they are used. The reactants for the process hereof are preferably admixed in a compatible aqueous solvent such as water which does not substantially hinder the desired phosphorylation reaction. Finally, sufficient base is added (preferably in an intermittent fashion during the reaction) to maintain the reaction mixture at a pH of at least about 8 during the entire reaction between the components of the mixture for enhancing the phosphorylation of the ascorbic acid derivatives. Maintenance of the pH level of the reaction mixture at the levels specified has been found to be important for achieving commercially feasible yields. Moreover, while the presence of a tertiary amine is advantageous when it is desired to produce a monoester product, this component may be omitted if it is desired to produce a phosphorylated diester.

In more detail, the ascorbic acid compound is preferably selected from the group consisting of ascorbic acid, the alkali and alkaline earth metal salts of ascorbic acid, the tertiary amine salts of ascorbic acid, and derivatives of ascorbic acid having a $C_6$ base-stable blocking group thereon. Examples of the latter type of compound are the 5, 6-acetal and 5, 6-ketal derivatives of ascorbic acid such as 5,6-O-benzylidene-L-ascorbic acid and 5,6-O-isopropylidene-L-ascorbic acid. In the most preferred form of the invention, the ascorbic acid reactant is selected from the group consisting of the four stereoisomers of the compound of the formula

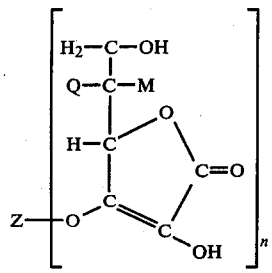   III.

where Z is selected from the group consisting of hydrogen, the alkali metals, the alkaline earth metals and the tertiary amines, n is the valence of Z, and Q and M are different and taken from the group consisting of —H and —OH, and compounds of the formula

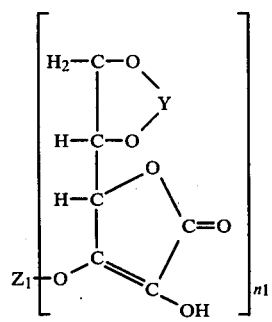   IV.

wherein $Z_1$ is selected from the group consisting of hydrogen, the alkali metals, alkaline earth metals and the tertiary amines, $n_1$ is the valence of $Z_1$, and Y represents cycloalkyls having from 5 to 7 carbon atoms or a group of the formula

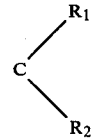   V.

where $R_1$ represents hydrogen, phenyl, furfural or alkyl groups of from 1 to 4 carbon atoms, and $R_2$ represents hydrogen or alkyl groups of from 1 to 4 carbon atoms.

The base added to the reaction mixture should be substantially miscible therein, of suitable base strength, and should not promote phase separation of the tertiary amine from the remainder of the reaction mixture. In this connection bases selected from the group consisting of the alkali metal hydroxides are particularly preferred. If it is desired to produce high yields of L-ascorbate 2-phosphate essentially free of diascorbyl 2,2'-phosphate, then the most preferred bases are potassium, rubidium or cesium hydroxides. Sodium hydroxide gives essentially quantitative 2-phosphorylation, but the reaction products may contain appreciable amounts of the phosphate diester. The phosphorylation reaction is somewhat slower in the presence of the moderately soluble lithium hydroxide. For this reason, lithium hydroxide leads to some unreacted ascorbate in the reaction mixture, and its use is therefore less desirable.

In order to enhance the production of the 2-phosphorylated monoester product hereof, it has been found that the amounts of reactants present and the reaction conditions should be controlled to a certain extent. For example, the amount of tertiary amine relative to the amount of ascorbic acid derivative is one factor which bears upon the ultimate yield. Specifically, approximately a fivefold excess of tertiary amine relative to the ascorbic acid derivative has been found to be advantageous. In terms of concentration ranges in the alkaline reaction medium, the tertiary amine should be added in an amount to achieve a concentration of from about 1.5 to 3 M, while the ascorbic acid derivative should be added in an amount such that the concentration thereof is from about 0.3 to 0.6 M. In the most preferred form, these ranges are respectively from about 2.2 to 2.6 M, and from about 0.4 to 0.5 M.

The amount of base added to the reaction mixture during the phosphorylation reaction can also be controlled in order to maximize production of desired phosphorylated ester products. For example, maintenance of the pH of the reaction mixture within the range of from about 8 to 13.5 during the phosphorylation reaction is preferred, while a range of from about 10 to 13, and most preferably from about 12 to 13, is advisable.

Finally, in the case of production of a 2-phosphated monoester product, the reaction temperature is preferably maintained at a level of from about $-10°$ to $10°$ C. Broadly, the reaction temperature should be the lowest at which the reaction mixture remains in liquid state and with no separation of the tertiary amine into a separate phase, and the above range has been found satisfactory in most instances. The base and phosphorylating agent should also preferably be added intermittently to the reaction mixture, as needed.

After the phosphorylation reaction has been completed, the 2-phosphated monoester can be isolated as the amorphous magnesium salt or as the crystalline tricyclohexylammonium salt (TCHAP). The tricyclohexylammonium group on the salt can be replaced with a cationic replacement member such as sodium, barium, potassium, magnesium, calcium, iron, cobalt and zinc. In preferred recovery procedures, the magnesium and tricyclohexylammonium salts are produced by the steps of passing the reaction mixture, after the phosphorylation reaction is complete, through a first ion exchange column in hydrogen ion form, washing the first column and collecting the effluent therefrom, and adding magnesium hydroxide to the effluent to form a magnesium salt of the ester. After removal of insoluble magnesium phosphate, the aqueous solution is evaporated to a small volume, and magnesium L-ascorbate is precipitated by addition of ethanol. The magnesium L-ascorbate 2-phosphate can be collected and purified by washing with 95% ethanol. The ethanolic washings remove magnesium chloride and magnesium diascorbyl 2,2'-phosphate. At this point, the isolated magnesium salt is virtually pure L-ascorbate 2-phosphate which contains traces of inorganic magnesium phosphate and chloride. To isolate crystalline TCHAP, the magnesium salt is passed through a second ion-exchange column in acid form, the second column is washed with water, and the effluent adjusted to alkaline pH by adding the appropriate amount of cyclohexylamine. At this point the tricyclohexylammonium salt (which in the case of an L-ascorbate 2-phosphate ester would be tricyclohexylammonium L-ascorbate 2-phosphate) is purified by crystallization and thereafter passed as an aqueous solution through a strongly acidic cation exchange resin in hydrogen ion form. The effluent from this procedure is adjusted to a basic pH using a salt such as sodium carbonate, and the resulting solution is evaporated. This yields a crop of sodium L-ascorbate 2-phosphate in excellent yield.

The mechanism by which the method hereof serves to produce high yields of 2-monophosphate esters of ascorbic acid is not completely understood. It is believed that pH maintenance throughout the reaction leads to rapid and essentially complete phosphorylation at the 2-position using a minimum amount of phosphorylating agents. Furthermore, the tertiary amine is believed to react with the initial product produced by the reaction between the ascorbic acid derivative and the phosphorous oxychloride (L-ascorbate 2-phosphorodichloridate) to produce an intermediate L-ascorbate 2-(pyridiniumphosphorochloridate) which is then rapidly hydrolyzed to give the desired monoester. If pyridine or another tertiary amine is absent from the reaction mixture, the dichloridate intermediate is believed to react with a second molecule of the ascorbic acid derivative to give the diascorbyl phosphate product. In this connection, use of a tertiary amine having an ionization constant of less than about $10^7$ (in water) probably lessens the destruction of phosphorylating agent in the reaction medium, and accordingly such amines are in general preferred.

The following examples illustrate the methods of the present invention, but nothing therein should be taken as a limitation upon the invention.

EXAMPLE 1

25 ml of pyridine (310 mmoles) and 100 ml of distilled water which had previously been boiled and purged with nitrogen gas were placed into a small beaker fitted with a pH electrode, a magnetic stirring bar and a nitrogen inlet tube. 12.3 gm (57.0 mmoles) of 5,6-O-isopropylidene-L-ascorbic acid (IAA) prepared according to the method described by K. G. A. Jackson and J. K. N. Jones, Can. J. Chem., 47 (1969), 2498, was added to the beaker, and the pH of the reaction mixture was adjusted to 13 by the addition of approximately 12 ml of 10 M aqueous potassium hydroxide. During pH adjustment nitrogen was bubbled through the reaction mixture, and the latter was cooled to approximately $-5°$ C. using a salt-ice bath. At this point, the concentration of pyridine and IAA in the reaction mixture were approximately 2.3 M and 0.44 M, respectively.

Phosphorous oxychloride (7.3 ml, 79.8 mmoles) was then pumped into the reaction mixture at a constant rate of 3 ml. per hour through plastic tubing (0.25 mm I.D.) using a syringe pump (Compact Infusion Model No. 975, Howard Apparatus Co., Inc., Melis, Mass.). The temperature of the reaction mixture was maintained within the range of from about $-5°$ to $5°$ C., and pH was maintained at a level of about 13 by periodic addition of 10 M aqueous potassium hydroxide. The total amount of 10 M potassium hydroxide added during the reaction was approximately 46 ml.

After the addition of phosphorous oxychloride was completed, water was added to the reaction mixture to make a volume of about 250 ml, and a 1 ml aliquot of this mixture was passed through a strongly acidic cation-exchange resin (15 ml) in the hydrogen-ion form. The ion-exchange column was thereafter washed with water (150 ml), the effluent made to a volume of about 250 ml, and a 1.0 ml aliquot of this latter solution was made to a 50 ml volume in water at pH 10.0.

The absorbance of the pH 10.0 solution was measured at 264 nm, and the percentage of 2-phosphorylation was estimated using the molar extinction coefficient of tricyclohexylammonium-L-ascorbate 2-phosphate ($\epsilon$ is equal to $16.0 \times 10^3$). The absorbance of the solution was 0.350, corresponding to 96.3% phosphorylation at the 2-position. The use of absorbance at 264 nm and pH 10 to estimate the degree of 2-phosphorylation is possible because (1) unreacted IAA and 3-phosphorylation would give lower extinction than 2-phosphorylation and (2) the molar extinction coefficient of the principal by-product in the phosphorylation of IAA, namely bis-(5,6-O-isopropylidene-L-ascorbyl) 2,2'-phosphate, equals $30.1 \times 10^3$ at pH 10, and thus its value is almost twice the magnitude of the molar extinction coefficient of L-ascorbate 2-phosphate. For these reasons, a high absorbance reading at pH 10 indicates a high degree of 2-phosphorylation. However, this uv data cannot be used to differentiate between L-ascorbate 2-phosphate, the phosphate diester, or other possible products, such as 2-pyrophosphate.

The amount of unreacted IAA in the reaction mixture was determined by iodometric titration. An aliquot (5.0 ml) of the total reaction mixture that had been made to 250 ml volume was diluted with 50 ml of 3% aqueous metaphosphoric acid, the mixture adjusted to pH 2 using concentrated hydrochloric acid, and the unreacted IAA was titrated with 0.1 M iodine solution. From the titer of a control sample of IAA, it was found that only 2.2% of the IAA had not been phosphorylated at its ene-diol group.

The number of phosphorylated components in the reaction mixture and their amounts were determined using high-pressure liquid chromatography (HPLC). The liquid chromatograph was model M-6000, Waters Associates, Milford, Mass., equipped with a uv detector (254 nm). Analyses were done using a 4 ft. by ⅛ in. stainless steel column packed with a pellicular, anion-exchange resin (type Bondapak AX/Corasil, Waters Associates) having a particle size of 37–50 microns. The column was operated at 25° C. and 500 lb. per sq. in. at a flow rate of 0.5 ml per minute using 0.1 M aqueous potassium dihydrogen phosphate adjusted to pH 4.4 with concentrated hydrochloric acid as the eluting solvent.

The reaction mixture was analyzed by HPLC both before and after hydrolytic removal of the isopropylidene group. In this connection, it is advantageous to examine the reaction mixture by HPLC before removal of the isopropylidene group since the resolution of the reaction mixture into its components is improved. On the other hand, HPLC analysis of the deacetonated products permitted the direct comparison of chromatographic properties of the reaction products with those of analytically pure samples of fully characterized materials [barium bis-(L-ascorbyl) 2,2'-phosphate and tricyclohexylammonium L-ascorbate 2-phosphate]. Accordingly, an aliquot (1.0 ml) of the total reaction mixture which has been previously diluted to 250 ml was evaporated under reduced pressure below 50° C. to remove pyridine. The residual alkaline solution was made to a volume of 25.0 ml with water, and an aliquot (1.0 ml) of the solution was combined with a 1.0 ml of a standard solution of barium L-ascorbate 2-sulfate dihydrate (100 mg in 100.0 ml of water) in a 100 ml volumetric flask. Triplicate 10.0 ul aliquots (each containing 2.34 nanomoles of L-ascorbate 2-sulfate) of the latter solution were injected into the chromatograph, and the amounts of 5,6-O-isopropylidene-L-ascorbate 2-phosphate and bis-(5,6-O-isopropylidene-L-ascorbyl) 2,2'-phosphate were determined from the areas under the peaks that had chromatographic mobilities (Ra) of 3.4 and 6.0, respectively, relative to the mobility of L-ascorbic acid. Errors due to slight differences in the injected volumes of reaction aliquots were cancelled by using the mean area found for 8 separate 10 ul injections of a solution obtained by diluting 1.0 ml of the internal standard solutions to 10.0 ml. The corrected area of 5,6-O-isopropylidene-L-ascorbate 2-phosphate found for the reaction mixture was assumed to give the same area as an equimolar amount of tricyclohexylammonium L-ascorbate 2-phosphate. The conversion of IAA to 5,6-O-isopropylidene-L-ascorbate 2-phosphate was calculated to be 97%.

The high conversion of IAA to the 2-phosphate ester was confirmed by HPLC assay after hydrolytic removal of the isopropylidene group. An aliquot (1.0 ml) of the reaction mixture that had been previously made to 250 ml was placed on a column of strongly acidic cation-exchange resin (15 ml) in the hydrogen ion form. The column was washed with water (150 ml), and the effluent made to volume (250 ml). Triplicate aliquots (10 ul) of the latter solution were injected, and the area under the peak at Ra=2.8 was integrated. A standard solution of analytically pure tricyclohexylammonium L-ascorbate 2-phosphate (0.5 g per liter) was injected (10 ul) to determine the response area of the instrument to the pure compound. The respective areas were used to calculate that 96.2% of the starting material (IAA) had been converted to L-ascorbate 2-phosphate. The chromatogram again showed that the reaction mixture contained only traces of the phosphate diester. In addition, the chromatograms showed the isopropylidene group was completely removed as soon as the reaction products were eluted from the ion-exchange column.

The remainder (247 ml) of the reaction mixture which had been analyzed by uv and HPLC, was passed through a column of strongly acidic cation exchange resin (600 ml) in the hydrogen ion form. The column was washed until the total effluent was 2000 ml. The absorbance of the column effluent at pH 10 and 264 nm showed a 93.4% recovery (53.1 mmoles) of the theoretical amount (57 mmoles) of L-ascorbate 2-phosphate expected for stoichiometric 2-phosphorylation of IAA. The column effluent (which was at pH 1.0), was allowed to stand 2 hr. at 25° C., and solid magnesium hydroxide (about 11 g) was added to adjust the pH to about 9.0. The mixture was then allowed to stand overnight at 5° C., and was filtered. Recovery of L-ascorbate 2-phosphate in the filtrate was 91.7%. The filtrate was next concentrated under reduced pressure to a volume of 50 ml, and the concentrate added to absolute ethanol (300 ml). The precipitated magnesium L-ascorbate 2-phosphate was collected by centrifugation and was washed with 95% ethanol (2×100 ml). High pressure liquid chromatographic examination of the ethanol washings showed that magnesium bis-(L-ascorbyl) 2,2'-phosphate was concentrated in the ethanolic washings, and that the solid residue contained only traces of the bis compound. The insoluble material was dried under vacuum to give 19.5 g of practically pure magnesium L-ascorbate 2-phosphate as a freeflowing powder (approximately 86% yield).

The supernatant from the centrifugation step and the ethanol washings were combined, and the resulting solution, which contained 6% of the theoretical amount of L-ascorbate 2-phosphate, was evaporated to dryness under vacuum. The solid residue was dissolved in water (50 ml). and barium hydroxide (2 g) was added to precipitated barium L-ascorbate 2-phosphate. The barium salt is very insoluble in water at pH 7, but it becomes soluble at pH 3–4. Barium L-ascorbate 2-phosphate was collected by centrifugation, and the supernatant was discarded (uv loss 0.24%). The precipitated barium L-ascorbate 2-phosphate was combined with the solid magnesium L-ascorbate 2-phosphate, and the mixture was passed through a strongly acidic cation exchange resin (600 ml) in the hydrogen ion form. The effluent from the column (2000 ml), which contained 82% of the theoretical amount of L-ascorbate 2-phosphate as determined by uv, was adjusted to pH 9 with cyclohexylamine, and concentrated under vacuum to a thick syrup. Addition of absolute ethanol and cooling overnight gave 18 g of crystalline tricyclohexylammonium L-ascorbate 2-phosphate (TCHAP) with m.p. 178–182° (dec) and $[\alpha]_D^{25} + 30°$ (c 1.0, $H_2O$). A second crop of crystals (3.1 g) brought the total yield of material to 21.1 g (70%). The mother liquors retained approximately 18% of L-ascorbate 2-phosphate, as determined by uv analysis.

The structure of TCHAP was determined by elemental analysis, u.v. spectroscopy, and by nuclear magnetic resonance spectroscopy. The elemental analysis of TCHAP showed the compound is indeed a monophosphate ester of L-ascorbate.

$C_{24}H_{48}O_9PN_3$ requires: C, 52.06; H, 8.74; P, 5.59; N, 7.59. Found: C, 51.95; H, 8.81; P, 5.34; and N, 7.39.

The elemental composition together with nmr and uv data leave little doubt that the main product isolated from the reaction of 5,6-O-isopropylidene-L-ascorbic acid with phosphorous oxychloride in a mixture of pyridine and alkali is L-ascorbate-2-phosphate.

EXAMPLE 2

Another phosphorylation reaction was conducted as described in Example 1 except the starting material was a 5,6-acetal derivative, 5,6-O-benzylidene-L-ascorbic acid. 57 millimoles of 5,6-O-benzylidene-L-ascorbic acid was used (m.p. 167–8°, prepared using the method described by S. Chladek and J. Smrt *Coll. Czech. Chem. Comm.*, 28 (1963) 1301; properties of compound given by T. M. Chu and W. R. Slaunwhite, Steroids, 12 (1968) 309). The degree of 2-phosphorylation was found to be 93% and the unreacted starting material 3%. The desired salt of L-ascorbate 2-phosphate (TCHAP) were obtained in substantially the same yield and degree of purity as described in Example 1.

EXAMPLE 3

The phosphorylation reaction was conducted as described in Example 1 except that L-ascorbic acid or D-isoascorbic acid (57 mmoles) was substituted for 5,6-O-isopropylidene-L-ascorbic acid. After addition of the phosphorous oxychloride, iodometric titration indicated 9–11% of unreacted L-ascorbic acid or D-isoascorbic acid was present in the reaction mixture. Afrer removal of the pyridine, uv absorption of the reaction mixture at 264 nm and pH 10 indicated 84% 2-phosphorylation for both isomeric ascorbic acids. The reaction mixture obtained starting with L-ascorbate was examined by high-pressure liquid chromatography, and showed the reaction mixture contained 73% L-ascorbate 2-phosphate and 10% bis-(L-ascorbyl) 2,2'-phosphate. Isolation of magnesium L-ascorbate 2-phosphate and tricyclohexylammonium L-ascorbate 2-phosphate (TCHAP) was done as previously described. The magnesium salt amounted to 17.1 g of a solid (65% yield, calculation based on a pentahydrate solid), while the TCHAP (m.p. 145–9°) totaled 16.1 g (51% yield).

EXAMPLE 4

Bis-(L-ascorbyl) 2,2'-phosphate diester was prepared as follows. 30 g (170.4 mmole) of L-ascorbic acid in deaerated water (300 ml) at 50° was stirred and solid barium hydroxide added until the pH of the reaction mixture reached 10.5. Phosphorous oxychloride (23.4 ml, 39.08 g, 254.0 mmole) was added dropwise over a period of 100 min. and the pH of the mixture was maintained at a level of about 9.5 to 10.5 by periodically adding solid barium hydroxide. The total barium hydroxide added was 190 g. The reaction mixture was maintained at 50° C., and the precipitated barium phosphate was removed by filtration. The filtrate was cooled (10° C.) overnight, and the crystalline solid was filtered off and dried over $P_2O_5$; yield 5.20 g (28.9%). Recrystallization gave analytically pure barium bis(L-ascorbyl) 2,2'-phosphate, m.p. 250°(dec), $[\alpha]_D^{25} + 65°$ (c 1.0 of sodium salt, $H_2O$): $C_{12}H_{12}O_{14}PBa_{3/2}$ requires: C, 23.35; H, 1.96; P, 5.02. Found: C, 23.46; H, 2.04; P, 4.70.

EXAMPLE 5

The tricyclohexylammonium cations of pure crystalline TCHAP can be replaced by other desired cations in order to produce other derivatives. Alternatively, the magnesium salt washed free of bis compound with ethanol can be used in place of TCHAP as the starting material. In this case an aqueous solution of tricyclohexylammonium L-ascorbate 2-phosphate (1.0 g) was passed through a column (15 ml) of strongly acidic cation exchange resin in the hydrogen ion form. The effluent was adjusted to pH 9 using sodium carbonate, and the resulting solution was evaporated to dryness. The yield of solid sodium L-ascorbate 2-phosphate (0.67 g) was 95% as determined by uv spectroscopy. Other salts, all of which were hygroscopic, were also prepared by this method. They included compounds containing the following replacement cations; barium (0.97 g) potassium, magnesium and calcium (0.92 g), iron (II), cobalt (II) and zinc.

EXAMPLE 6

In order to determine the effect of increasing pH upon phosphorylation of 5,6-O-isopropylidene-L-ascorbic acid (IAA), the following experiment was undertaken. The general reaction scheme described in Example 1 was followed, with an initial reaction mixture which contained 6.15 g (28 mmoles) of IAA (initially 0.44 M), 10 ml of pyridine (initiall about 1.9 M) and 55 ml aqueous potassium hydroxide. Phosphorous oxychloride (6.1 g, 40 mmoles) was added dropwise and the pH of the reaction mixture was maintained by adding 10 M potassium hydroxide as needed. The temperature of all reactions was held within the range of from about −5° to +5° C. Five separate reactions were conducted at pH levels of 8, 10, 12, 13 and 14 respectively. The phosphorylated products recovered from the respective reactions were analyzed using uv, high pressure liquid chromatography techniques and iodine titration in the manner described in connection with Example 1, in order to determine the extent of phosphorylation at the 2-position, as well as respective amounts of mono and diesters produced.

The results of these analyses on the reaction products are set forth in the following Table I:

TABLE I

Phosphorylation of 5,6-O-Isopropylidene-L-Ascorbic Acid (IAA)

| Reaction No. | pH | $A_{264}$ | Unreacted IAA, % | Phosphorylation at 2-position, % | IAA 2-Phosphate |
|---|---|---|---|---|---|
| 1 | 8  | 0.245[a] | 24[b] | 67[c] | 72[d] |
| 2 | 10 | 0.265    | 23    | 73    | 70    |
| 3 | 12 | 0.290    | 10    | 80    | 85    |
| 4 | 13 | 0.338    | 6.7   | 93    | 89    |
| 5 | 14 | 0.265    | 1.2   | 73    | 60    |

[a]Every reaction mixture gave, after evaporative removal of pyridine, $\lambda_{max}$ at 258 nm and 264 nm at pH 7 and 10, respectively.
[b]Determined by iodometric titration of an aliquot (5.0 ml) of a reaction mixture made to volume (250.0 ml) with water. Prior to titration with 0.1 N iodine solution, the aliquot was diluted with 40 ml of 3% aqueous metaphosphoric acid, and the mixture adjusted to pH 2.0 with hydrochloric acid. The iodine solution was standardized using L-ascorbic acid.
[c]Determined from the absorbance of a reaction mixture at pH 10 using the extinction of L-ascorbate 2-phosphate at 264 nm ($\epsilon = 16.0 \times 10^3$ at pH 10.0). The principal by-product in all reaction mixtures, bis-(L-ascorbyl) 2,2'-phosphate, was shown to have $\epsilon = 30.1 \times 10^3$ at pH 10. Pyridine was removed from each reaction mixture before reading its absorbance.
[d]See Footnote [d] in Table II, p. 24.

The uv data given above demonstrates that as the pH of the reaction medium increased from 8 to 13, the degree of 2-phosphorylation increased from 67% to 93%, while unreacted IAA decreased from 24% to 6.7%. The uv absorption maximum of all the reaction mixtures 1-5 occurred at 258 nm at pH 7, which shows the principal phosphorylation reaction occurred at the 2-OH rather than the 2-OH. The uv absorption maximum for L-ascorbate 3-phosphate would be expected at 238 nm at pH 7.0, which is the absorption maximum of L-ascorbyl 3-phenylphosphate (A. S. Bond, et al., *Arch. Biochem. Biophys.*, 1972, 153, p. 207).

TABLE II

HPLC Analysis of Phosphorylation Reaction Mixtures Obtained Starting With 5,6-O-Isopropylidene-L-Ascorbic Acid (IAA)

| Reaction No. | pH | Area of Standard, $cm^2$ | Area of IAA-2-P, $cm^2$ | Corrected Area of IAA-2-P, $cm^2$ | Yield IAA-2-P |
|---|---|---|---|---|---|
| 1 | 8  | 5.61[a] | 15.59[b] | 16.3[c] | 72[d] |
| 2 | 10 | 5.69    | 15.41    | 15.8    | 70    |
| 3 | 12 | 5.73    | 18.68    | 19.1    | 85    |
| 4 | 13 | 6.14    | 21.03    | 20.0    | 89    |
| 5 | 14 | 5.82    | 13.50    | 13.5    | 60    |

[a]The respective reaction mixtures after completion of the described phosphorylation reaction were made to volume (250 ml) with water. An aliquot (1.0 ml) was evaporated to remove pyridine, the residual solution adjusted to 25.0 ml, and a 1.0 ml aliquot of the solution added to a 10.0 ml volumetric flask containing 2.34 nmoles of barium L-ascorbate 2-sulfate. Injections onto the chromatograph were 10 microliters.
[b]IAA-2-P = 5,6-O-isopropylidene-L-ascorbate 2-phosphate.
[c]Corrected for volume variation which occurred during injection of the 10 ml sample. The average area of response for the internal standard in 8 separate injections (10 ml each) of a solution of barium L-ascorbate 2-sulfate dihydrate (2.34 nanomoles) was 5.35 $cm^2$.
[d]Yield calculated from fact that the area of 20.2 $cm^2$ under the peak for IAA-2-P represented a 89.7% conversion of IAA to IAA-2-P during the phosphorylation reaction. Acid hydrolysis of the isopropylidene group from IAA-2-P followed by injection into the liquid chromatograph gave L-ascorbate 2-phosphate with a response area equivalent to 89.7% yield as determined from the area response given by an analytically pure sample of tricyclohexylammonium L-ascorbate 2-Phosphate (TCHAP). Extinction of IAA-2-P was assumed to equal that of TCHAP.

Phosphorous-31 nuclear magnetic resonance measurements on the reaction mixture obtained at pH 10 (Table I, Reaction No. 2) verified the presence of only two organic, phosphorylated products in the mixture. The major 31 P resonance signal was observed at 2.79 ppm downfield from the signal of an external reference standard of 50% aqueous phosphoric acid, whereas the minor component was observed at 0.4 ppm downfield from the standard. The major 31 P signal was identical with that of the pure tricyclohexylammonium L-ascorbate 2-phosphate added to the reaction mixture. A third 31 P-resonance signal was also observed in the reaction mixtures which was identified as orthophosphate.

EXAMPLE 7

The effect of the most preferred tertiary amine, i.e., pyridine, on the phosphorylation reactions hereof was studied by way of the following experiment. In addition, the effect of using triethylamine in place of pyridine was examined. Reactions Nos. 6–9 were carried out as described in footnote "a" of Table III hereunder, with the concentrations of pyridine being varied in the respective reactions.

TABLE III

Effect of the Initial Pyridine Concentration on the Yield of L-Ascorbate 2-Phosphate Starting from 5,6-O-Isopropylidene-L-Ascorbate

| Reaction No. | Pyridine Initial Vol. % | 2-Phosphatelation, % | L-ascorbate 2-phosphate, % | Phosphate Diester, % |
|---|---|---|---|---|
| 6 | 15.2 (1.9M)[a] | 93[b] | 89[c] | 4.9[d] |
| 7 | 18.2 (2.3M)    | 96    | 97    | <1    |
| 8 | 22.3 (2.8M)    | 96    | 97    | <1    |
| 9 | 26.8 (3.3M)    | 91    | 85    | —     |

[a]All reactions run at pH 13.0 and 0° C. The reaction mixtures contained 6.15g IAA (28 mmoles) in approximately 66 ml of a mixture of aqueous potassium hydroxide and pyridine. Initial concentration of IAA prior to addition of POCl₃ was about 0.44M. Phosphorous oxychloride (40 mmoles, 1.4 eq) was added dropwise, and the pH of the reaction mixture was maintained at 13 by adding 10M potassium hydroxide solution as needed.
[b]Determined from the absorbance of a reaction mixture at 264 nm and pH 10 after removal of pyridine using a strongly acidic cation exchange resin in the hydrogen ion form.
[c]Determined by HPLC after hydrolytic removal of the isopropylidene blocking group.
[d]Bis-(L-ascorbyl) 2,2'-phosphate.

The data in Table III demonstrates that at the most preferred pH level of from about 12 to 13, the quantity of pyridine should be controlled in order to depress the formation of the phosphate diester and thereby to realize almost quantitative yields (96%) of L-ascorbate 2-phosphate. For economic reasons, one would of course use the lowest concentration of pyridine giving the desired effect. Even though 5% of bis-(L-ascorbyl) 2,2'-phosphate in a reaction mixture appears small (Reaction No. 6, Table III), this amount of contaminant can cause problems by retarding the crystallization of tricylohexylammonium L-ascorbate 2-phosphate (TCHAP). Furthermore, the phosphate diester was difficult to separate from the desired TCHAP by fractional crystallization. It is believed that if too little pyridine is used, then the amount of bis-(L-ascorbyl) 2,2' phosphate in the reaction mixture is increased. On the other hand, if too large a quantity of pyridine is added, the reaction mixture can separate into two phases and the amount of phosphorous oxychloride required to completely react with the starting material IAA is greatly increased.

In a separate set of three experiments, reaction No. 7 in Table III was repeated using triethylamine for pyridine on an equimolar basis, and using 3 levels of phosphorous oxychloride (1.4, 1.8 and 3.0 equivalents). In these reactions unreacted IAA was 21%, 19% and 20%, respectively, while the degree of 2-phosphorylation was 62, 67 and 62%, respectively. HPLC assay of the reaction mixture obtained using 1.4 eq. at POX₃ showed the mixture contained 52% L-ascorbate 2-phosphate and 13% diascorbyl 2,2'-phosphate.

The effect of complete elimination of tertiary amine from the phosphorylation reaction is shown in Table IV. The yield of the phosphate diester increased from 3% at pH to 32% at pH 13, whereas the amount of unreacted starting material decreased from 38% to <1%.

Table IV

Phosphorylation of 5,6-O-Isopropylidene-L-Ascorbic Acid in the Absence of Tertiary Amine

| Reaction No. | Reaction pH | Unreacted IAA, 90 | IAA 2-P, % | Bis-(IAA) 2,2'-P, % |
|---|---|---|---|---|
| 10 | 8[d] | 28[b] | 43[c] | 3.2[c] |
| 11 | 10 | 43 | 42 | 9.3 |
| 12 | 12 | 11 | 51 | 22 |
| 13 | 13 | 1 | 51 | 32 |

[a]Each reaction run as described in Example 7 with the exception of amine and pH.
[b]Determined by iodometric titration of an aliquot (5.0 ml) of a reaction mixture made to volume (250.0 ml) with water. Prior to titration with 0.2 N iodine solution, the aliquot was diluted with 40 ml of 3% aqueous metaphosphoric acid, and the mixture adjusted to pH 2.0 with hydrochloric acid. The iodine solution was standardized using L-ascorbic acid.
IAA 2-P and bes-(IAA) 2,2'phosphate = 5,6-0-isopropylidene-L-ascorbate 2-phosphate and bis -(5,6-0-isopropylidene-L-ascorbate)2,2'-phosphate, respectively, Determined by HPLC assuming ther molar area responses of the 5,6-acetonated species equal those of pure tricyclohexylammonium L-ascorbate 2-phosphate and barium bis-(L-ascorbyl) 2,2'-phosphate.

The above experiments indicate that both high pH together with relatively high concentrations of pyridine in the phosphorylating reaction are preferred for high conversion of 5,6-O-isopropylidene-L-ascorbate to its 2-phosphate ester. In this connection it is important that the high pH be maintained in the reaction mixture during the phosphorylation reaction, as opposed to only initially.

However, if it is desired to produce the diascorbyl 2,2'-phosphate starting with IAA or other ascorbic acid derivatives, then no tertiary amine should be used (see Table IV) and the pH should be maintained at a level above about 10 (see also Example IV). In addition, as discussed above (see Example 5), this reaction can advantageously be carried out at relatively high temperatures (on the order of 30° to 60° C.) and in the presence of barium hydroxide. These conditions speed up the phosphorylation reaction, and provide a reaction mixture from which the phosphate diester is more easily isolated.

EXAMPLE 8

The phosphorylation of 5,6-O-isopropylidene-L-ascorbic acid (IAA) using different bases was examined as follows. 6.15g of IAA was dissolved in a mixture of water (50ml) and pyridine (12.5 ml) under $N_2$ bubbling, and the mixture was adjusted to pH 13 by addition of approximately 6 ml of 10M aqueous sodium hydroxide, potassium hydroxide, rubidium hydroxide, or cesium hydroxide. The phosphorylation reaction was conducted essentially as described in Example 1 using 1.4 equivalents of phosphorous oxychloride (constant reaction pH=13, reaction temperature −5° to 5°). The reaction mixtures obtained using the different bases were analyzed as previously described, and the results are given in Table V:

TABLE V

Effect of Inorganic Base on the Yield of L-ascorbate Z-phosphate Starting From 5,6-O-Isopropylidene-L-Ascorbate

| Reaction No. | Metal Hydroxide | Unreacted IAA, % | 2-Phosphorylation, % | L-Ascorbate 2-phosphate, % | Phosphate Diester, % |
|---|---|---|---|---|---|
| 14a | Lithium | — | 74 | 48 | — |
| 14b | Sodium | 2 | 91 | 67 | 24 |
| 15 | Potassium | 0.4 | 93 | 94 | 3 |
| 16 | Rubidium | 0.5 | 93 | 94 | 2 |
| 17 | Cesium | 0.4 | 93 | 94 | 2 |

The above data indicated potassium, rubidium and cesium hydroxide are the most preferred bases if one wishes to produce 2-phosphate esters of ascorbic acid. Strong bases which are of low solubility in water, such as lithium hydroxide, barium hydroxide, magnesium hydroxide, and calcium hydroxide, do not perform as well in the phosphorylation reaction, since excess water is introduced with the base during maintenance of the reaction pH.

EXAMPLE 9

This experiment was undertaken to study the effect of usng L-ascorbic acid (AA) as opposed to IAA in the phosphorylation reaction. The data from this series of comparative tests is set forth in Table VI below and indicates that ascorbic acid can be used, but that the yields were somewhat lower as compared with use of IAA. In addition, in two runs (Nos. 22 and 23), methods described in the prior art were repeated wherein (No. 22) no pyridine was used and the pH was not maintained at the initial levels achieved, and wherein (No. 23) the pH during the reaction was in the range of from about 5.7 to 4.5. In both of these cases the yields were poor, i.e., 24 and 18% respectively.

The above tests are summarized in the following table, along with the reaction conditions:

TABLE VI

Phosphorylation of L-Ascorbate

| Reaction No. | Starting Material | Reaction pH | Pyridine, Initial Volume, % | Unreacted Starting Material, % | 2-phosphorylation, % | L-ascorbate 2-phosphate, % |
|---|---|---|---|---|---|---|
| 18 | AA[a] | 11 | 15.2 | — | 67[c] | 53[d] |
| 19 | AA | 12.2 | 21.1 | 1.7[b] | 90 | 68 |
| 20 | AA | 13 | 18.2 | 8.1 | 84 | 73(65)[g] |
| 21 | IAA | 13 | 18.2 | 1.6 | 96 | 96 |
| 22 | AA[e] | 13 to 9.2 | 0 | 35.2 | 63 | 24(37% bis)[h] |

TABLE VI-continued

Phosphorylation of L-Ascorbate

| Reaction No. | Starting Material | Reaction pH | Pyridine, Initial Volume, % | Unreacted Starting Material, % | 2-phosphorylation, % | L-ascorbate 2-phosphate, % |
|---|---|---|---|---|---|---|
| 23 | AA[f] | 5.7 to 4.5 | 40 | 36.0 | 37 | 18(24% bis)[h] |

[a]Reaction mixture (except reaction nos. 22 and 23) initially contained 5.0g of L-ascorbic acid (AA) or 6.15g of 5,6-O-isopropylidene-L-ascorbic acid (IAA) in distilled water (56 ml) containing an amount of potassium hydroxide to adjust the reaction pH to the desired value, and then pyridine (10, 12.5 or 15 ml) was added to give a mixture containing about 15,18,or 21 volume-% pyridine. Phosphorous oxychloride (6.1g, 1.4 eq.) was added dropwise at 0°–5° and the pH of the reaction mixture was maintained by dropwise addition of 10M potassium hydroxide.
[b]See footnote "b", Table IV.
[c]See footnote "c", Table I.
[d]Determined by HPLC usong the area of a standard solution of pure tricyclohexylammonium L-ascorbate 2-phosphate.
[e]Repeat of Example 3 given in Nomura, et al., German Patent No. 1,805,958 (1969). Ascorbic acid (8.3g) and calcium hydroxide (11.5g) dissolved in water (30 ml). Phosphorous oxychloride (7.5g) was added dropwise to the reaction mixture at 0° C. over a period of 90 min.
[f]Repeat of Reaction No. 8 in Table I of Nomura, et al., Chem.Pharm. Bull. 19,(1971) 1422. Ascorbic acid(4.1g) and pyridine (12 ml) were dissolved in water (15 ml). Phosphorous oxychloride (4.2g) was added dropwise over a period of 90 min. whole maintaining the temperature at 0° C.
[g]Phosphorous oxychloride increased form 1.4 to 1.6 equivalents (based on moles of AA). This resulted in a decrease in yield from 73 to 65%.
[h]Principal product in both reactions was bis-(L-ascorbyl) 2,2'-phosphate.

A study of the above results will show that as pH level is increased and maintained, 2-phosphorylation is increased. In addition, paper chromatographic examination of the phosphorylated reaction mixture obtained starting with L-ascorbate reveals a more intense red-colored spot (ferric chloride visualizing agent) in the dimer or diphosphate region of the chromatogram than observed in that region for chromatograms of reaction mixtures starting from 5.6-O-isopropylidene-L-ascorbate (IAA). The highest degree of 2-phosphorylation achieved for L-ascorbate was 90% as compared with 96% for IAA (Reaction Nos. 19 and 21, Table VI). The lower degree of 2-phosphorylation of L-ascorbate is also indicative of more diphosphate esters in the reaction mixtures obtained by starting with L-ascorbate, since the L-ascorbate phosphate diesters have an approximately 6% lower extinction coefficient than L-ascorbate 2-phosphate at pH 10 and 264 nm.

Finally, the importance of maintenance of pH at a relatively high level during the phosphorylation reaction is demonstrated by runs 22 and 23 wherein the results were very poor.

In reaction 22 the pH, although initially high, was allowed to drop during the reaction, and no pyridine was present; only a 24% yield was achieved. In reaction 23, although pyridine was used, the pH level was never on the alkaline side and it fell from 5.7 to 4.5 during the reaction, giving a yield of 18%.

Having thus described the invention, what is claimed as new and desired to be secured by Letters Patent is:

1. A method of preparing a 2-phosphated ester of 5,6-isopropylidene-L-ascorbic acid which comprises the steps of:
   admixing a quantity of 5,6-isopropylidene-L-ascorbic acid, a quantity of pyridine, and a sufficient amount of an alkali metal hydroxide to initially elevate the pH of the admixture to a level of about 12–13, in water,
   said 5,6-isopropylidene-L-ascorbic acid being present in said admixture at a concentration of from about 0.3 to 0.6 molar, said pyridine being present in said admixture at a concentration of from about 1.5 to 3.0 molar; and adding a quantity of phoshorous oxychloride to said admixture, and reacting the components of said admixture at a temperature of from about —10 to 10° C., and, during said reaction, adding additional quantities of said phosphorous oxychloride and said hydroxide to said admixture, said hydroxide being added for maintaining said pH at a level of from about 12–13 throughout the entirety of the reaction, in order to form primarily a 2-phosphated ester of said 5,6-isopropylidene-L-ascorbic acid.

2. The method as set forth in claim 1 wherein said acid is present at a concentration of from about 0.4 to 0.5 molar.

3. The method as set forth in claim 1 wherein said pyridine is present at a concentration of from about 2.2 to 2.6 molar.

* * * * *